US012220727B2

(12) United States Patent
Cheyns et al.

(10) Patent No.: US 12,220,727 B2
(45) Date of Patent: Feb. 11, 2025

(54) FLEXIBLE ULTRASOUND ARRAY

(71) Applicants: IMEC VZW, Leuven (BE);
KATHOLIEKE UNIVERSITEIT LEUVEN, Leuven (BE)

(72) Inventors: David Cheyns, Heffen (BE); Yongbin Jeong, Heverlee (BE); Xavier Rottenberg, Kessel-Lo (BE)

(73) Assignees: IMEC VZW, Leuven (BE);
KATHOLIEKE UNIVERSITEIT LEUVEN, Leuven (BE)

( * ) Notice: Subject to any disclaimer, the term of this patent is extended or adjusted under 35 U.S.C. 154(b) by 781 days.

(21) Appl. No.: 17/438,705

(22) PCT Filed: Mar. 12, 2020

(86) PCT No.: PCT/EP2020/056587
§ 371 (c)(1),
(2) Date: Sep. 13, 2021

(87) PCT Pub. No.: WO2020/182926
PCT Pub. Date: Sep. 17, 2020

(65) Prior Publication Data
US 2022/0152654 A1    May 19, 2022

(30) Foreign Application Priority Data
Mar. 14, 2019 (EP) .................... 19162702

(51) Int. Cl.
*B06B 1/06* (2006.01)
*B06B 1/02* (2006.01)
*A61B 8/00* (2006.01)

(52) U.S. Cl.
CPC .......... *B06B 1/0629* (2013.01); *B06B 1/0207* (2013.01); *B06B 1/0685* (2013.01); *A61B 8/4488* (2013.01); *B06B 2201/76* (2013.01)

(58) Field of Classification Search
CPC ... B06B 1/0629; B06B 1/0207; B06B 1/0685; B06B 1/0622; B06B 8/4488; B06B 2201/76
See application file for complete search history.

(56) References Cited

U.S. PATENT DOCUMENTS

| 6,541,896 B1 | 4/2003 | Jones et al. |
| 8,277,380 B2 | 10/2012 | Daft et al. |

(Continued)

FOREIGN PATENT DOCUMENTS

| CN | 104364742 A | 2/2015 |
| CN | 106028942 A | 10/2016 |

(Continued)

OTHER PUBLICATIONS

European Search Report for Application No. 19162702.5-1001, dated Aug. 8, 2022, 6 pages.

(Continued)

*Primary Examiner* — Emily P Pham
(74) *Attorney, Agent, or Firm* — MOSER TABOADA (57) ABSTRACT

The present invention provides a flexible ultrasound transducer (1) for an ultrasound monitoring system for examining a curved object. The ultrasound transducer (1) comprises an integrated circuit structure (7) and a multi-layered structure (2), said multi-layered structure (2) comprising an array (3) of ultrasound transducing elements (3a) arranged in a first layer structure (4) and configured for generating ultrasonic energy propagating along a main transducer axis Z and an array (5) of control circuits (5a) arranged in a second layer structure (6), and wherein the array (5) of control circuits and the integrated circuit structure (7) are configured for operating the array (3) of ultrasound transducing elements in said first layer structure (4), Further, the multi-layered structure (2) comprises at least one flexible layer (8, 9) arranged so that the bending flexibility of the multi-layered (Continued)

structure (2) permits the ultrasound transducer (1) to form a continuous contact with said curved object during operation.

13 Claims, 7 Drawing Sheets

(56) References Cited

U.S. PATENT DOCUMENTS

| | | |
|---|---|---|
| 2004/0113524 A1 | 6/2004 | Baumgartner et al. |
| 2007/0066902 A1* | 3/2007 | Wilser ................. B06B 1/0292 600/459 |
| 2008/0315331 A1 | 12/2008 | Fisher et al. |
| 2011/0181149 A1 | 7/2011 | Shikata |
| 2011/0291207 A1* | 12/2011 | Martin ................. H10N 30/04 257/E21.53 |
| 2013/0040264 A1 | 2/2013 | Scurtescu |
| 2015/0087988 A1* | 3/2015 | Lee ................. B06B 1/0622 600/459 |
| 2015/0180370 A1* | 6/2015 | Huang ................. H03H 3/0072 310/300 |
| 2017/0110504 A1 | 4/2017 | Panchawagh et al. |

FOREIGN PATENT DOCUMENTS

| | | |
|---|---|---|
| CN | 106999985 A | 8/2017 |
| EP | 2401966 A1 | 1/2012 |
| EP | 3217171 A1 | 9/2017 |
| JP | 2012015680 A | 1/2012 |
| JP | 2019503095 A | 1/2019 |
| WO | WO-2010/109205 A2 | 9/2010 |

OTHER PUBLICATIONS

International Search Report and Written Opinion for Application No. PCT/EP2020/056587 dated May 12, 2020.

* cited by examiner

FLEXIBLE ULTRASOUND ARRAY

TECHNICAL FIELD

The present inventive concept relates to the field of ultrasound imaging.

More particularly it relates to a flexible ultrasound transducer comprising an array of ultrasound transducing elements.

BACKGROUND

Large 2D arrays of ultrasound arrays have several applications in the medical market and for consumer electronics. Examples are medical imaging, gesture recognition, directed sound, fingerprint detection and mid-air haptics.

The standard structure of a micromachined ultrasound transducer (MUT) is known in the art. A small drum is made, with a suspended membrane on top of a small cavity. The dimensions of this cavity in combination with the stiffness of the membrane will determine the resonance frequency of a particular MUT. As an example, the MUT may be driven by the piezo-electric effect (pMUT). By applying an AC electric field at the resonance frequency across a piezoelectric material, a stress difference between the piezo-electric material and the membrane is generated, and this will induce a vibration and the emission of an acoustical wave. Typical frequencies are in the range of 50 kHz to 20 MHz. This translates into wavelengths ranging from 1 cm down to <100 um for airborne waves. Applications that use beam-forming to create a focal spot in emission or to image a small spot in receiving, require larger arrays of ultrasound transducers working together.

The optimal pitch between subsequent elements in the array for ideal beam forming techniques is wavelength/2. Depending on the used stack, this means that the pitch between elements will be close to the dimensions of a discrete transducer. The consequence is a high density of pMUT elements, with almost no place between the elements.

Furthermore, a small circuit might be required next to each individual pMUT, for either setting the correct phase, reading out the phase/amplitude. This circuit might be relatively complex, and there could be no room in the same plane as the pMUTs.

There is thus a need in the art for improved designs of ultrasound transducers that may be manufactured in large arrays. Further, ultrasound transducers that are manufactured on flat rigid substrates may not be fit for scanning curved objects. The operator has to move and press the flat transducer against the curved object to be examined, which leads to difficulties in reproduction of images etc. Thus, there is also a need in the art for ultrasound transducers allows for improved examination of curved objects.

SUMMARY

It is an object of the invention to at least partly overcome one or more limitations of the prior art. In particular, it is an object to provide a flexible ultrasound transducer that may be used for examining curved objects.

As a first aspect of the invention, there is provided a flexible ultrasound transducer for an ultrasound monitoring system for examining a curved object, wherein said ultrasound transducer comprises an integrated circuit structure and a multi-layered structure, said multi-layered structure comprising an array of ultrasound transducing elements arranged in a first layer structure and configured for generating ultrasonic energy propagating along a main transducer axis (Z) and an array of control circuits arranged in a second layer structure, and wherein the array of control circuits and the integrated circuit structure are configured for operating the array of ultrasound transducing elements in said first layer structure; and wherein said a multi-layered structure further comprises at least one flexible layer arranged so that the bending flexibility of the multi-layered structure permits the ultrasound transducer to form a continuous contact with said curved object during operation.

The flexible ultrasound transducer is for transducing ultrasound into an object and may be used in an ultrasound monitoring system. Such system may also comprise separate processing means for processing the resultant echo signals obtained from the object that is examined, display means for displaying an image obtained by the ultrasound transducer and separate communication means for transferring information from the processing means to the display means.

The multi-layered structure of the ultrasound transducer is a stack of different layers or layer structures. Each layer structure may comprise different sub-layers. The integrated circuit structure may be a part of the multi-layered structure, i.e. it may form one of the layers of the multilayers, or it may be arranged as discrete elements attached to the multilayer structure, such as to the bottom layer. The bottom layer may be a backplane flexible layer.

The function of the integrated circuit structure can be multiple, such as providing signals for excitation of the ultrasound transducing elements, reading the readout of the signals of the ultrasound transducing elements. Thus, the integrated circuit structure may be configured for processing the resultant echo signals obtained from the object that is examined. Moreover, the integrated circuit structure may also provide for wireless communication with other units, such as a display system, of an ultrasound monitoring system.

The array of ultrasound transducing elements is arranged in a first layer structure. The array may be a two-dimensional array. The surface area of the array may be at least 100 cm$^2$, such as at least 400 cm$^2$.

The flexible ultrasound transducer may be in the form of a sheet. The sheet may have a first outer surface and a second outer surface, oppositely arranged of each other, i.e. having normal vectors pointing in two different and parallel directions. The outer layers of the multi-layered structure may form the first and second outer sheets, respectively. The surface area of the sheet, such as the surface area of the first or second outer surface may be at least 100 cm$^2$, such as at least 400 cm$^2$.

The first layer structure may form part of or constitute a "frontplane" of the flexible ultrasound transducer.

A single ultrasound transducing element may be a piezoelectric micromachined ultrasound transducer (pMUT). A pMUT may comprise a flexible membrane on top of a small cavity. The dimensions of the cavity in combination with the stiffness of the membrane may determine the resonance frequency of the pMUT. As an example, the pMUT may be driven by the piezo-electric effect, i.e. a stress difference between a piezo-electric material and the membrane may be generated by applying an AC electric field at the resonance frequency across a piezoelectric material.

As an alternative, a single ultrasound transducing element may be a capacitive MUT (cMUT), in which the actuation is performed by an air gap in the MUT and electrodes at each side of the air gap.

The resonance frequency of an ultrasound transducing element may be in the range of 50 kHz to 20 MHz. This translates into wavelengths ranging from 1 cm down to <100 um.

The array of ultrasound transducing elements is further configured for generating ultrasonic energy that propagates in a main direction, i.e. along a transducer axis Z. The position of a different layer and layer structure of the multilayer may in the present disclosure be defined as being "axially above" or "axially below" another layer and layer structure. The terms "axially" refers to transducer axis Z, and a layer or layer structure being arranged axially above another layer or layer structure is thus arranged at position that is further along in the positive Z direction. Hence, if the transducer axis Z points vertically upwards, then "axially above" corresponds to "vertically above" and "axially below" corresponds to "vertically below".

The array of control circuits is arranged in a second layer structure. The second layer structure may be a single layer. The control circuits and the integrated circuit structure are thus used for operating the ultrasound transducing elements.

The second layer structure may be arranged axially below the first layer structure. Thus, the second layer structure may form part of or constitute a "backplane" of the flexible ultrasound transducer.

The second layer structure may comprise thin-film semi-conductive materials, such as IGZO (Indium Gallium Zinc Oxide) and/or LTPS (Low Temperature Poly Silicon). Thus, the second layer structure may comprise IGZO and/or LTPS based control circuits.

Further, the multi-layered structure comprises at least one flexible layer. The flexible layer or layers are arranged in the structure so that the multilayer and the whole ultrasound transducer becomes flexible and permits the ultrasound transducer to form a continuous contact with a curved object during examination. Thus, due to the flexible layer, the ultrasound transducer may conform to the curved object during examination.

The at least one flexible layer may be at least one of a backplane flexible layer and a frontplane flexible layer.

A flexible membrane in a pMUT may form one of the flexible layers. However, the ultrasound transducing elements may comprise at least one flexible layer other than a flexible layer associated or part of an ultrasound transducing element for generating the ultrasound, such comprising at least one flexible layer other than the flexible layer or membrane that is part of the pMUT discussed above.

The flexible ultrasound transducer is for examining a curved object. The curved objects suitable may be objects having a curvature with a bend radius of less than 20 cm, such as less than 10 cm. Having at least one flexible layer within the multilayer structure makes it possible for the flexible ultrasound transducer to bend and conform to such a curved object and an outer layer of the multilayer structure may thus form a continuous contact with the curved object. As an example, all layers of the multilayer structure may flex upon contact with the curved object.

The first aspect of the invention is based on the insight that a flexible ultrasound transducer may be created by incorporating flexible layers in a multi-layer structure in which the array of ultrasound transducing elements and the array of control circuits are arranged in separate planes. The inventors have found that it may be a disadvantage to have a control circuit vibrating together with the ultrasound transducing elements. Therefore, the array of ultrasound transducing elements may be provided in a frontplane whereas the array of control circuits may be provided in a backplane of the flexible ultrasound transducer. This is further advantageous in that it allows for separate processing of frontplanes and backplanes, i.e. different layers or layer structures of the multi-layered structure may originate from different suppliers.

When processing the frontplane and backplane independently from each other manufacturing constraints may be avoided. Hence, any temperature constrains for processing of backplane is not limited by the frontplane thermal properties.

Further, since the array of ultrasound transducing elements and the array of control circuits are arranged in separate planes, it allows for using a high density of ultrasound transducing elements, such as piezoelectric micromachined ultrasound transducers (pMUTs), in the array together with complex control circuits in an array below the ultrasound transducing elements.

The design of the flexible ultrasound transducer also makes it possible manufacture a flexible ultrasound transducer having a large area, such as having an area that is at least 100 cm$^2$, such as at least 400 cm$^2$.

Since the whole ultrasound transducer is flexible, it may allow for conforming around curved objects during ultrasound imaging. The flexible ultrasound transducer of the present disclosure may thus be used for medical imaging, gesture recognition on curved substrates and non-destructive inspections around curved substrates. The curved objects or substrates that can be examined may thus be parts of the human body, such as an arm or a leg, but also other objects such as door handles and the dashboard of a car.

The flexible ultrasound transducer may be used on an object that is moving, such as on a moving human body part. Thus, the flexible ultrasound transducer may be glued or fastened onto a human body.

In embodiments of the first aspect, each ultrasound transducing element in the array of said first layer structure is connected with an individual control circuit of the array of said second layer structure.

Thus, an individual control circuit may be configured for controlling a single ultrasound transducing element.

As an alternative, the individual control circuits may be arranged for controlling more than one ultrasound transducing element, such as at least two, such as at least four, ultrasound transducing elements. As an example, the individual control circuits may be arranged for controlling a 2×2 subarray of ultrasound transducing elements.

In embodiments of the first aspect, the second layer structure is arranged axially above a backplane flexible layer of the at least one flexible layer.

The control circuits may thus be processed directly on a backplane flexible layer, such as onto a flexible polymer layer.

The integrated structure or circuits may comprise any standard or custom device, such as Complementary Metal Oxide Semiconductor (CMOS) devices, to support specific functionalities, e.g. wireless ASIC or Digital Signal Processors (DSP).

In embodiments of the first aspect, the integrated circuit structure comprises a plurality of Application Specific Integrated Circuits (ASIC). As an example, at least one ASIC may support a plurality of individual control circuits.

The control circuits may thus be driven by a plurality of dedicated ASICs, and a single ASIC may thus be configured for supporting or driving a plurality of individual control circuits.

An ASIC may be specially built for performing a specific function or a specific task and may be configured for exciting the ultrasound transducing elements but also for reading output signals from the array of ultrasound transducing elements. The plurality of ASIC may also be configured for wireless communication with other parts of an ultrasound monitoring system.

As an example, the plurality of Application Specific Integrated Circuits (ASIC) may be mounted as discrete elements axially below said backplane flexible layer.

Consequently, the ASICs may be mounted directly onto the backplane flexible layer, using e.g. chip-on-flex techniques.

However, as an alternative, the ASICs may be incorporated in one of the layers of the multi-layered structure.

In embodiments of the first aspect, the first layer structure comprises an array of piezoelements arranged on a frontplane flexible layer, a bulk layer comprising internal walls so as to define an array of cavities in the bulk layer, wherein an ultrasound transducing element in the array is defined by one of said piezoelements, a cavity of said array of cavities and a portion of the frontplane flexible layer arranged in between the piezoelement and the cavity.

The frontplane flexible layer may be one of the flexible layers that are arranged so that the bending flexibility of the multi-layered structure permits the ultrasound transducer to form a continuous contact with said curved object during operation.

The frontplane flexible layer may be arranged directly on top of the bulk layer. Further, the array of cavities and the array of piezoelements may be arranged so that there is one single cavity associated with each piezoelement. As an example, the cavities may be arranged under the piezoelements.

The ultrasound transducing elements may be or comprise MUTs that are configured to be electronically actuated.

An ultrasound transducing element may thus be driven by the piezo-electric effect. By applying an AC field, near or at the resonance frequency across the piezoelement, a vibration of the frontplane flexible layer may be generated and thereby an emission of an acoustical wave. The dimensions of the cavities may be adjusted to achieve different resonance frequencies. The frontplane flexible layer may thus function as a membrane in an ultrasound transducing element.

The ultrasound transducing elements may thus be or comprise piezoelectric micromachined ultrasound transducers (pMUTs).

As a further example, the ultrasound transducing elements may be or comprise capacitive ultrasound transducers (cMUTs).

In embodiments of the first aspect, the array of control circuits comprises an array of thin film transistors (TFT).

A TFT may comprise a semiconductor, such as IGZO (Indium Gallium Zinc Oxide) and/or LTPS (Low Temperature Poly Silicon), as well as a dielectric layer and metallic contacts. These may be deposited on a substrate, such as polymer on a glass wafer.

There may be a single TFT associated with a single ultrasound transducing element. Thus, the flexible ultrasound transducer may comprise a TFT backplane and a separate pMUT frontplane.

In embodiments of the first aspect, the multi-layered structure further comprises an acoustic backing layer arranged axially below said first layer structure or reducing the acoustic transmission directed away from said curved object during operation.

An acoustic backing layer may thus be added to the stack in order to manage the wave shot that is directed away from object that is examined. An acoustic backing layer thus reduces the problems coming from acoustic emission in the wrong direction.

As an example, the acoustic backing layer may be arranged axially below the second layer structure. Thus, the acoustic backing layer may be arranged axially below the array of control circuits.

Furthermore, the acoustic backing layer may be an acoustic damping layer or an acoustic reflection layer in the form of a Bragg stack. The Bragg stack may comprise multiple layers of alternating high and low acoustic impedance materials.

Consequently, the acoustic backing layer may have an absorptive nature, in which the acoustic wave is substantially damped or absorbed, or a reflective nature, in which the acoustic wave is reflected.

An acoustic damping layer may be obtained by using a material in which the emitted ultrasound loses its power.

An acoustic reflection layer may be obtained by using an acoustic Bragg stack (Bragg reflector), comprising multiple layers of alternating high and low acoustic impedance materials. This may aid in reflecting the ultrasound wave. The Bragg stack may be designed using quarter wavelength rules. Thus, each of the multiple layers of the Bragg stack may have a thickness corresponding to one quarter of the wavelength for which the Bragg stack is designed.

The multiple layers of alternating high and low acoustic impedance materials may flexible, while providing band gap reflection at the target acoustic application frequency. Band gap engineering can further be used to allow broadband function.

In embodiments of the first aspect, the flexible ultrasound transducer further comprises a top flexible layer arranged as an outermost layer axially above the first layer structure.

The top flexible layer may be arranged so that the bending flexibility of the multi-layered structure permits the ultrasound transducer to form a continuous contact with said curved object during operation.

It may be advantageous in having a flexible layer as the axially outermost layer, such as axially on top of the other layers of the multi-layer structure, since such a material may bend more easily during operation of the ultrasound transducer. The outermost layer will experience the highest flexure or bending stress, and it may be useful to avoid having the ultrasound transducing elements and the control circuits as the outermost layer, since these may be more sensitive to flexure.

One or all of the at least one flexible layers may comprise a polymer, such as a polyimide.

In embodiments of the first aspect, the multi-layered structure has a bending flexibility such that the flexible ultrasound transducer may be bent with a radius of curvature that is less than 5 cm.

The bend radius may be defined when bending in positive or negative Z-direction, i.e. the direction along the main transducing axis. The minimum radius of curvature may be less than 5 cm, such as 1-4 cm.

According to another aspect of the present inventive concept, there is provided a method for producing a flexible ultrasound transducer according to any previous claim, comprising the steps of a) arranging said second layer structure comprising an array of control circuits axially above a backplane flexible layer that is temporarily bonded to a first rigid substrate;
b) arranging said first layer structure comprising an array of ultrasound transducing elements;
c) forming the multi-layered structure of the flexible ultrasound transducer; and
d) removing said first rigid substrate.

This aspect may generally present the same or corresponding advantages as the former aspect.

Step a) may comprise arranging the second layer structure comprising an array of control circuits directly onto a backplane flexible layer.

Step b) may comprise providing a bulk layer and forming cavities in the bulk layer, e.g. using a photo-litho patternable adhesive, laminating a frontplane flexible layer over the bulk layer and arranging an array of piezoelements on top of the frontplane flexible layer.

Step d) may be a step of delaminating the backplane flexible layer from the first rigid substrate.

In embodiments of the second aspect, the first layer structure is built up on top of the second layer structure. Consequently, step b) of arranging the first layer structure may be performed on top of the second layer structure arranged in step a). Step c) may therefore be a part of step b).

Thus, the sublayers of the first layer structure, such as a bulk layer, the front flexible layer, and the piezoelements, may be arranged sublayer by sublayer on top of the second layer structure.

In embodiments of the second aspect, the first layer structure is temporarily bonded to a second rigid substrate, and wherein the method comprises removing said second rigid substrate before forming the multi-layered structure of the flexible ultrasound transducer.

Thus, the first layer structure may be built on a separate rigid substrate. This is advantageous in that the first layer structure and the second layer structure may be manufactured in different manufacturing processes that are optimized for the first and second layer structure, respectively. The first and second layer structures may thus be supplied from different providers and the method may then comprise forming the multilayer structure by arranging the pre-fabricated first layer structure on top of the pre-fabricated second layer structure after delamination from their rigid substrates.

BRIEF DESCRIPTION OF THE DRAWINGS

The above, as well as additional objects, features and advantages of the present inventive concept, will be better understood through the following illustrative and non-limiting detailed description, with reference to the appended drawings. In the drawings like reference numerals will be used for like elements unless stated otherwise.

DETAILED DESCRIPTION

Figure 1A:
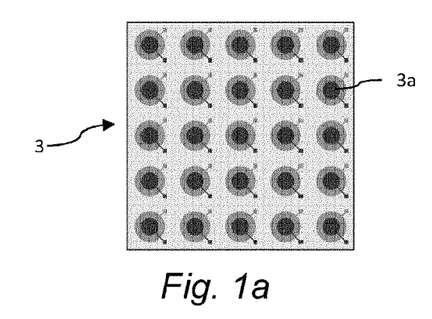
FIG. 1a is an illustration of an array of ultrasound transducing elements.

The present invention relates to a flexible ultrasound transducer 1 for an ultrasound monitoring system for examining a curved object. The transducer has an integrated circuit structure 7 and a multi-layered structure 2, and an array 3 of ultrasound transducing elements is arranged in a first layer structure of the multilayer structure. A top view of a 5×5 array 3 of ultrasound transducing elements 3a is schematically shown in FIG. 1a. The ultrasound transducing elements are 3a in this example pMUT elements. The optimal pitch between elements 3a in the array 3a may be half of the emittance wavelength of the ultrasound transducer. The array 3 of ultrasound transducing elements 3a is further configured for generating ultrasonic energy propagating along a main transducer axis (Z), which in FIG. 1a is perpendicular to the plane in which the array is arranged.

Figure 1B:
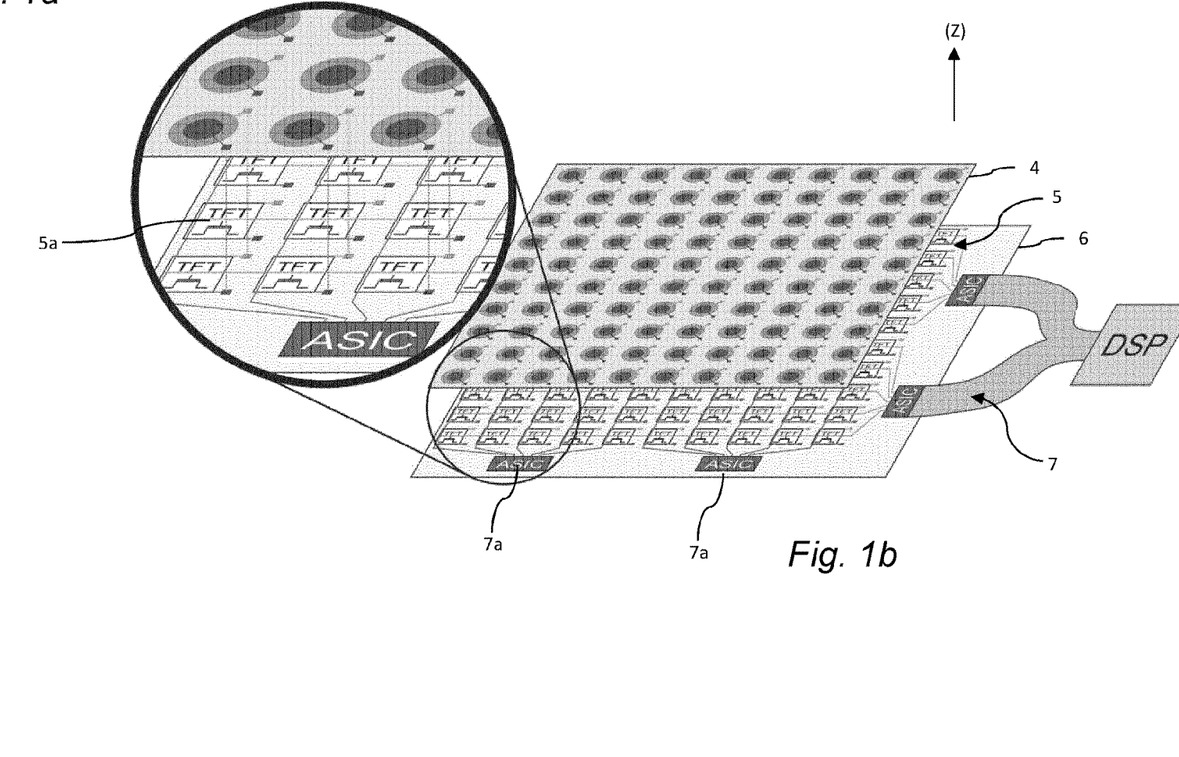
FIG. 1b is an illustration of a first and second layer structure in an ultrasound transducer.

The array 3 of ultrasound transducing elements 3a in the first layer structure 4 is operated by the use of an array 5 of control circuits 5a and the integrated circuit structure 7. As illustrated in FIG. 1b, the array 5 of control circuits 5a is arranged in a second layer structure 6 other than the first layer structure 4. The array 5 of control circuits 5a is used for e.g. setting the correct phase and for reading out the phase and/or amplitude of the echo signal from the object being examined.

In this example, the first layer structure 4 forms a frontplane of the multilayer and the second layer structure 6 forms a backplane, in which the frontplane is arranged axially above the backplane. The backplane or the second layer structure 6 is in this example a thin-film transistor (TFT) backplane which is arranged so that each individual transducer element 3a is connected to an individual control circuit 5a, or TFT circuit.

The control circuits 5a are connected to the integrated circuit structure 7, which in this example is realized as a plurality of Application Specific Integrated Circuits (ASIC) 7a. The ASICs 7a are in this case arranged in a separate plane axially below the second layer structure 6, and each individual ASIC is configured for supporting a plurality of control circuits 5a, such as more than 20, such as more than 100 control circuits 5a. The function of the ASICs 7a may be multiple, such as generating signals for excitation of the ultrasound transducing elements 3a, reading out the phase and/or amplitude of the echo signal from the object being examined and/or for wireless communication with other parts of the ultrasound transducer.

Furthermore, the ultrasound transducer comprises at least one flexible layer arranged so that the bending flexibility of the multi-layered structure 2 permits the ultrasound transducer) to form a continuous contact with a curved object, such as an arm or a leg, during operation. This will be further discussed in relation to FIGS. 2-7 below.

Figure 2A:
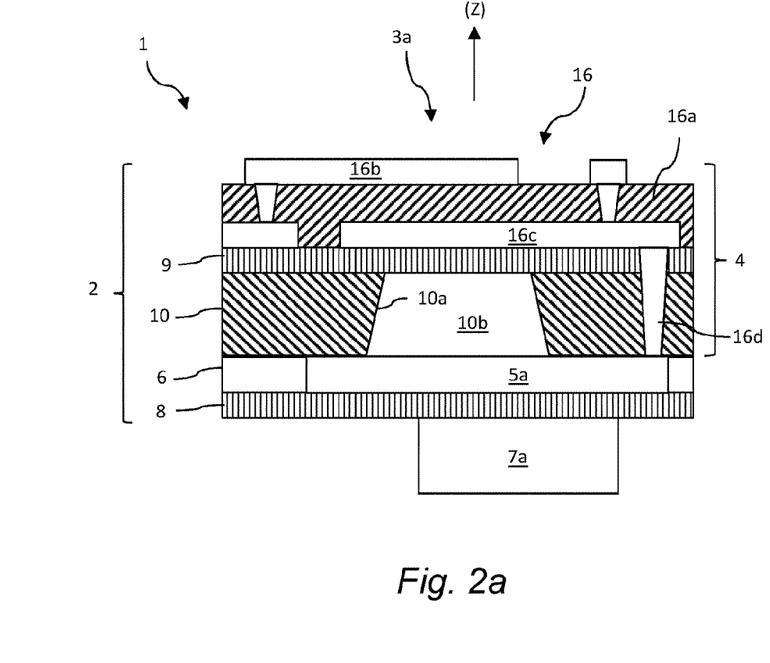
FIGS. 2a-d show illustrative embodiments of the layer structure in a flexible ultrasound transducer.

FIG. 2a shows an embodiment of the layer structure of the multi-layered structure 2 of the flexible ultrasound transducer 1. The multilayer structure 2 comprises a first layer structure 4 arranged axially on top of a second layer structure 6. The second layer structure 6 comprises an array 5 of control circuits 5a in the form of an array of TFT circuits, that has been processed axially on top of a backplane flexible layer 8. This backplane flexible layer is a polymer layer with desired flexibility, such as a polymer layer comprising or consisting of polyimide.

The ultrasound transducing elements 3a are arranged within the first layer structure 4 and configured for generating ultrasonic energy propagating along a main transducer axis Z. The first layer structure 4 comprises a frontplane flexible layer 9, which function as a membrane in the individual ultrasound transducing elements 3a. The frontplane flexible layer 9 may be the same layer for all individual ultrasound transducing elements 3a in the array 3 of ultrasound transducing elements. The frontplane flexible layer is arranged between a bulk layer 10 and an array of piezoelements 16. The bulk layer 10 comprises internal walls 10a so as to define an array of cavities 10b in the bulk layer 10 and a piezoelement 16 comprises a piezoelectric material 16a arranged between a top metal layer 16b and a bottom metal layer 16c. There is further an electrical connection 16d arranged between the control circuits 5a and the bottom metal layer 16c. The electrical connection 16d is arranged through the backplane flexible layer 9 and the bulk layer 10 and is used by the control circuit 5a and the integrated circuit 7 to apply an AC electric field over the piezoelectric material 16a. In FIG. 2a, only a bottom connection 16d between the bottom metal layer 16c the TFT 5a is shown, but also the top metal layer 16b may be connected to the TFT 5a. As an alternative, either the bottom metal 16c or the top metal 16b may be a common contact for the full array of ultrasound transducing elements. In that case, the top metal 16b may be connected to a ground signal.

Consequently, an individual ultrasound transducing element 3a in the array 3 is defined by one of the piezoelements 16, a cavity 10b of the array of cavities and the portion of the frontplane flexible layer 9 that is arranged between the piezoelement 16 and the cavity 10b. By applying an AC electric field at the resonance frequency across the piezoelectric material 16a, a stress difference between the piezoelectric material and the frontplane flexible layer 9 is generated, and this will induce a vibration and the emission of an acoustical wave. Typical frequencies are in the range of 50 kHz to 20 MHz. This translates into wavelengths ranging from 1 cm down to <100 um.

The integrated circuit 7 comprises a plurality of ASICs 7a. In this embodiment, the individual ASICs 7a are mounted at the opposite side of the backplane flexible layer 8 than the side of the backplane flexible layer 8 onto which the second layer structure 6 is processed using a chip-on-flex technique. Thus, the ASICs 7a are arranged axially below the backplane flexible layer 9. In one embodiment, the connection between an ASIC 7a and the control circuits 5a it supports is made through the backplane flexible layer 8. In another embodiment, the connection is realised using flexible PCB connectors that go around the backplane flexible layer 9. It is also possible to have the second layer structure 6 arranged axially on top of the first layer structure 4, such as on top of the top metal 16b. Such a solution may require the second flexible layer 6 having through holes for the ultrasound emitted by the ultrasound transducing elements.

Figure 2B:
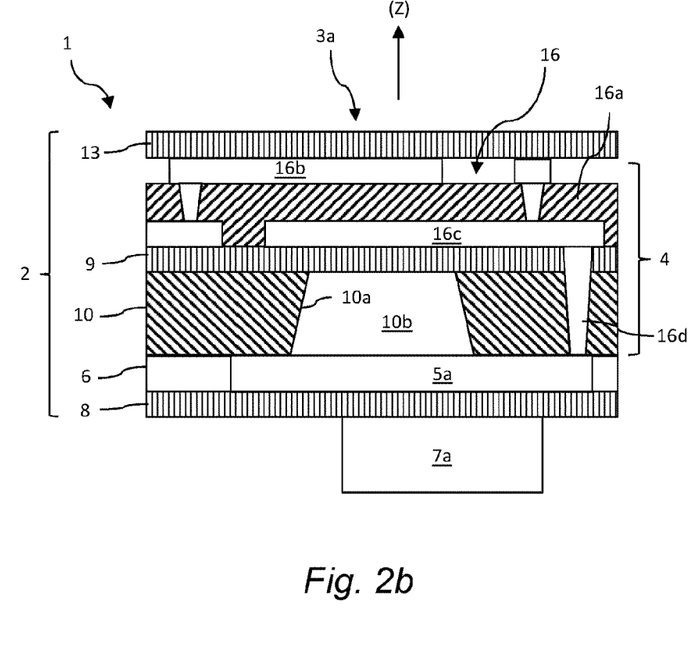

FIG. 2b shows a further schematic illustration of an embodiment of a flexible ultrasound transducer 1. The flexible ultrasound transducer 1 of FIG. 2b has the same layer structure and function in the same way as the transducer discussed in relation to FIG. 2a, but has an additional top flexible layer 13 arranged as an outermost layer axially above the first layer structure 4. This may protect the ultrasound transducing elements 3a and the TFTs 5a during bending of the multi-layered structure 2, since the outermost layer, in this case the top flexible layer 13, may experience the most bending stress during bending. The top flexible layer may have the same thickness and/or consist of the same material as the backplane flexible layer 8.

Figure 2C:
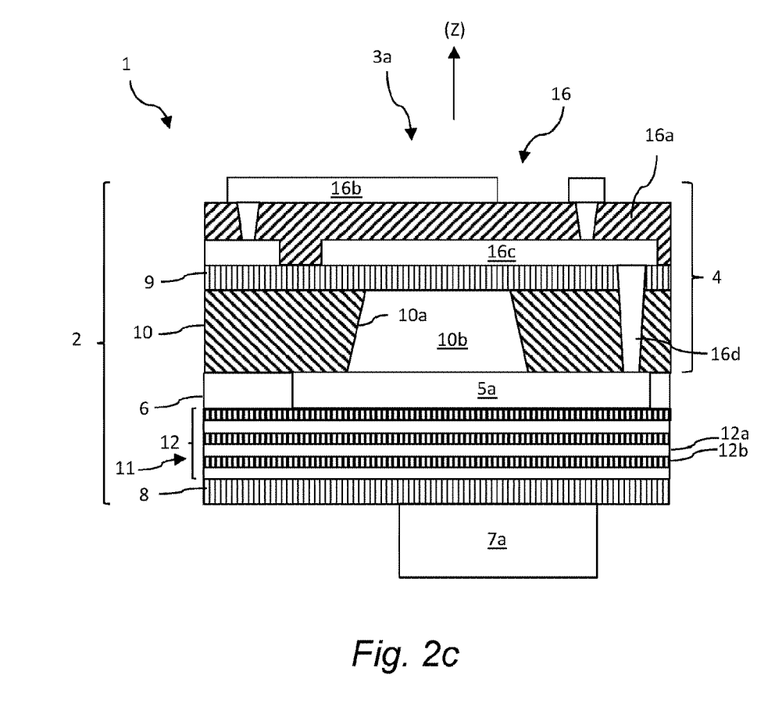

FIG. 2c shows a further schematic illustration of an embodiment of a flexible ultrasound transducer 1. The flexible ultrasound transducer 1 of FIG. 2c has the same layer structure and function in the same way as the transducer discussed in relation to FIG. 2a, but has an acoustic backing layer 11 arranged axially below the first 4 and second 6 layer structure. The acoustic backing layer 11 is for reducing the acoustic transmission directed away from the object during operation of the ultrasound transducer 1. The acoustic backing layer is in the embodiment shown in FIG. 2c in the form of Bragg stack 12 that comprises multiple layers of alternating high 12a and low 12b acoustic impedance materials. The Bragg stack 12 is a "quarter wave mirror", i.e. designed with the alternating acoustic impedance materials 12a, 12b having a transmissive layer thickness corresponding to one quarter of the wavelength for which the Bragg stack 12 is designed. Using a Bragg stack 12, the acoustic power directed in the negative Z- direction may via constructive interference be reused for emission in the right direction, i.e. in positive Z direction. The Bragg stack 12 may also be made flexible, i.e. one or both layers of alternating high 12a and low 12b acoustic impedance may be made of a flexible material.

As an alternative, the acoustic backing layer 11 may be an acoustic damping layer, in which the power of the emitted ultrasonic wave is reduced.

Figure 2D:
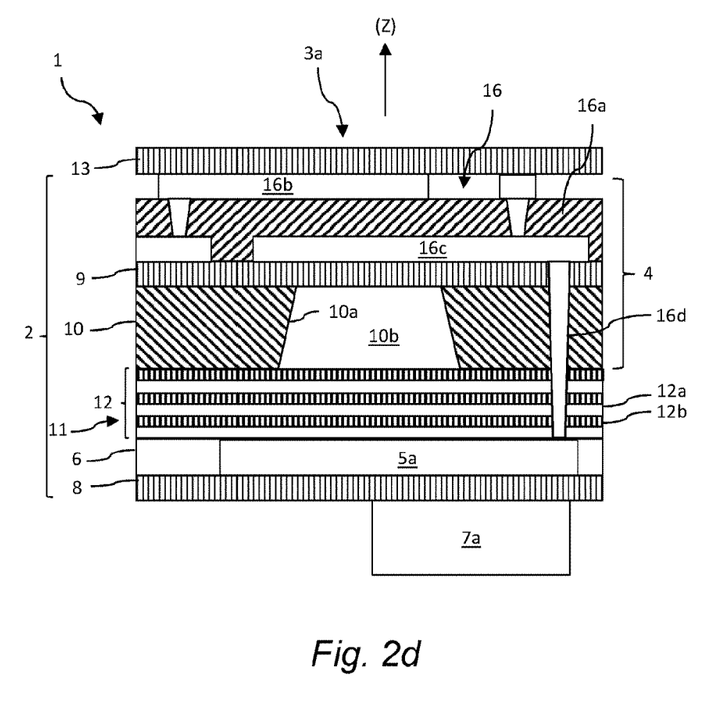

FIG. 2d shows a further schematic illustration of an embodiment of a flexible ultrasound transducer 1. The flexible ultrasound transducer 1 of FIG. 2d has the same layer structure and function in the same way as the transducer discussed in relation to FIG. 2d, but the acoustic backing layer 11 in the form of a Bragg stack 12 is instead arranged axially between the first 4 and second 6 layer structures. Further, similar to what is shown in FIG. 2b, there is a top flexible layer 13 arranged as the outermost layer, axially above all other layers in the multi-layered stack 2. The top flexible layer may be as discussed in relation to FIG. 2b above.

The use of at least one flexible layer, such as incorporating the backplane flexible layer 8, the frontplane flexible layer 9 and/or the top flexible layer 13 in the multilayer structure 2, gives the multi layered structure 2 and the whole flexible ultrasound transducer 1 a flexibility such that it has a bending flexibility such that the flexible ultrasound transducer 1 may be bent with a radius of curvature that is less than 5 cm. this allows for use e.g. when examining curved body parts. Thus, the flexible ultrasound transducer 1 may be wrapped around an arm or a leg, and may further provide for ultrasonic imaging during motion of the object that is being examined, such as during motion of an arm or a leg of a person being examined.

Figure 6:
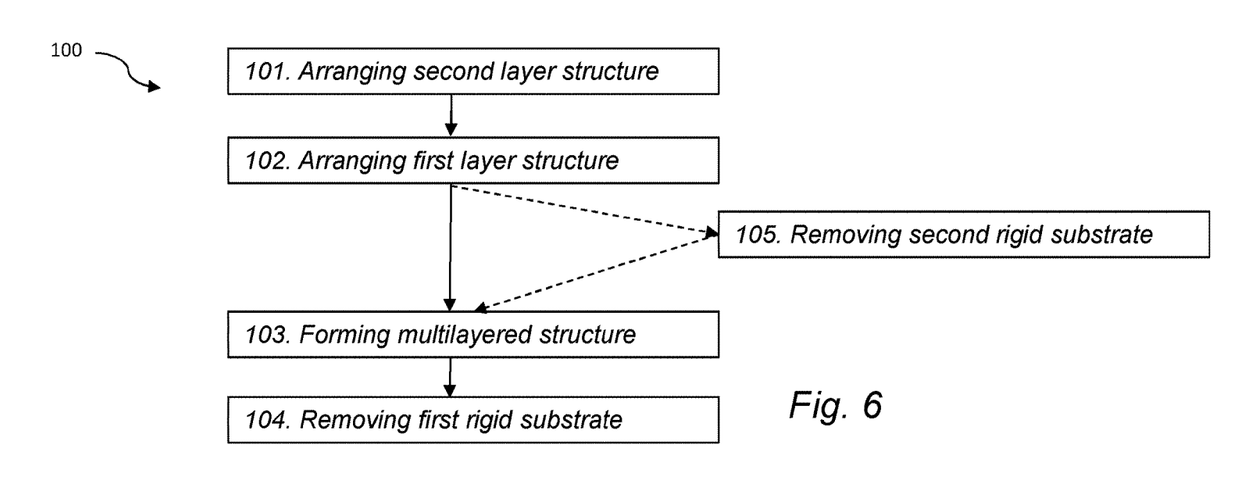
FIG. 6 show a general outline for the process steps in the method for manufacturing a flexible ultrasound transducer.

FIGS. 3-5 show different methods 100 for producing or manufacturing a flexible ultrasound transducer 1 according to the present disclosure. The method comprises the below general method steps a)-d), further illustrated in FIG. 6:

a) arranging 101 said second layer structure 6 comprising an array 5 of control circuits 5a axially above a backplane flexible layer 8 that is temporarily bonded to a first rigid substrate 14;

b) arranging 102 said first layer structure 4 comprising an array 3 of ultrasound transducing elements 3a;

c) forming 103 the multi-layered structure 2 of the flexible ultrasound transducer; and d) removing 104 said first rigid substrate 4.

Step a) of arranging 101 the second layer structure may also comprise arranging an acoustic backing layer 11 as discussed herein above between the second layer structure 6 and the backplane flexible layer 8, or on top of both the second layer structure 6 and the backplane flexible layer 8.

The first layer structure 4 may be temporarily bonded to a second rigid substrate 15, and the method 100 may also comprise removing 105 the second rigid substrate 15 before forming the multi-layered structure 2 of the flexible ultrasound transducer 1.

Figure 3A:
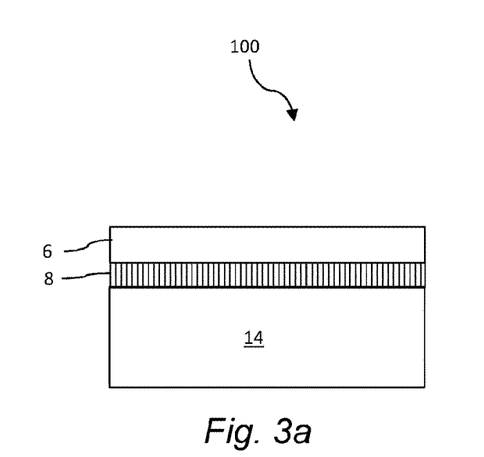
FIGS. 3a-f show an illustrative embodiment of a method for manufacturing a flexible ultrasound transducer.

FIGS. 3a-3f schematically shows an embodiment of the method 100 for producing a flexible ultrasound transducer 1 in which the first layer structure 4 is built up on top of the second layer structure 6. First, as seen in FIG. 3a, a TFT circuit backplane of the second layer structure 6 is processed on a backplane flexible layer 8 that is temporarily bonded to a first rigid substrate 14. The backplane flexible layer 8 may consist of or comprise polyimide. The TFT circuit backplane may comprise IGZO (Indium Gallium Zinc Oxide) and/or LTPS (Low temperature polysilicon) TFTs. Thus, the array 5 of control circuits (5a) is arranged axially above a flexible layer 8.

Figure 3B:
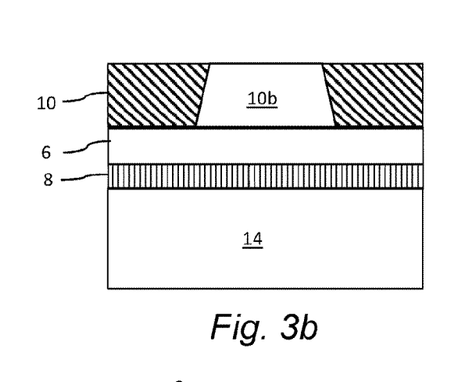

A bulk layer 10 in the form of a photo-litho patternable adhesive is deposited on top of the second layer structure 6 and cavities 10b in the bulk layer are formed using photo-lithography, as shown in FIG. 3b.

Figure 3C:
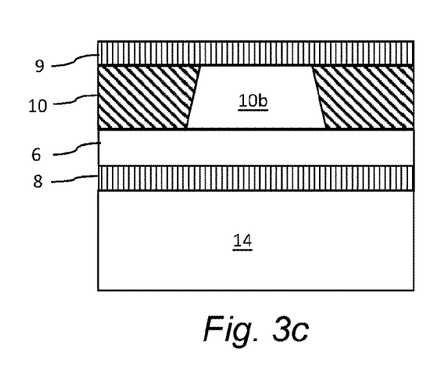

As illustrated in FIG. 3c, a frontplane flexible layer 9 is then laminated axially on top of the bulk layer 10, and as discussed herein above, the frontplane flexible layer functions as the membrane in the ultrasound transducing elements.

Figure 3D:
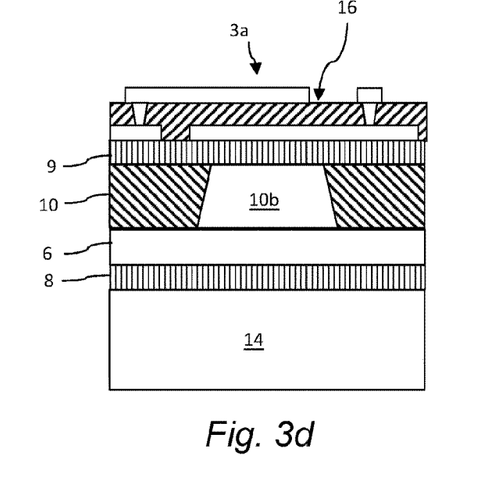

As illustrated in FIG. 3d, the piezoelectric elements 16 are fabricated axially on top of the frontplane flexible layer 9, thereby the forming individual ultrasound transducing elements 3a in the form of pMUTs of the flexible ultrasound transducer 1.

Figure 3E:
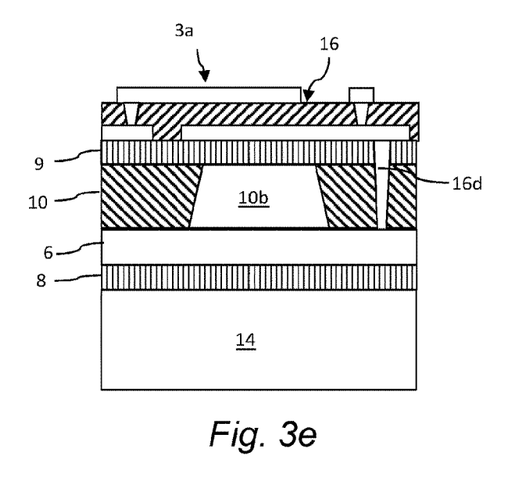

Further, a connection 16d from the piezoelectric element 16 is fabricated through the frontplane flexible layer 9 and the bulk layer 10 to the second layer structure 6, thereby making a connection between the TFTs and the pMUT. This is illustrated in FIG. 3e.

Figure 3F:
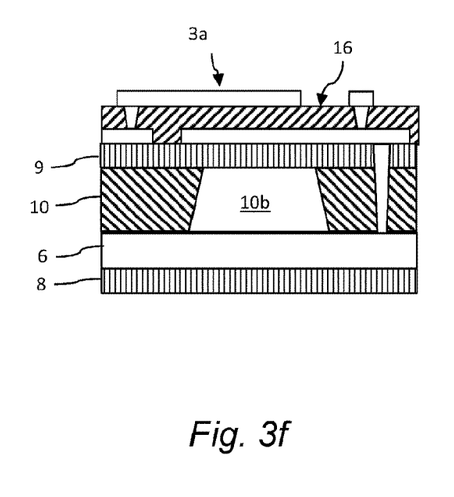

As a last step, the backplane flexible layer 8 is delaminated from the a first rigid substrate 14, thereby providing the flexible ultrasound transducer 1, as illustrated in FIG. 3f.

FIGS. 4a-4f schematically shows an alternative embodiment of the method 100 for producing a flexible ultrasound transducer 1 in which the first layer structure 4 and the second layer structure 6 are processed independently on different rigid substrates.

Figure 4A:
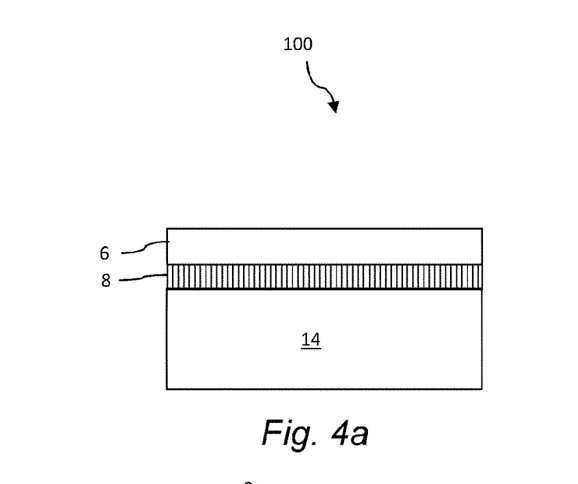
FIGS. 4a-f show an illustrative embodiment of a method for manufacturing a flexible ultrasound transducer.
Figure 4B:
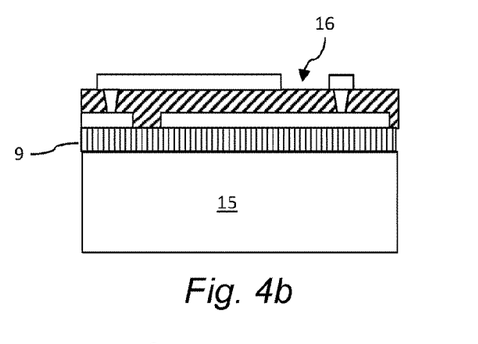

The second layer structure 6 in the form of a TFT control circuit backplane is processed on a backplane flexible layer 8, which is temporarily bonded on a first rigid carrier substrate 14, see FIG. 4a. Further, the first layer structure 4 including the ultrasound transducers 3a in the form of pMUTs is processed independently from the second layer structure 6 on a frontplane flexible layer 9, which function as the membrane in the ultrasound transducers 3a. The frontplane flexible layer 9 is temporarily bonded to a second rigid carrier substrate 15, as seen in FIG. 4b.

Figure 4C:
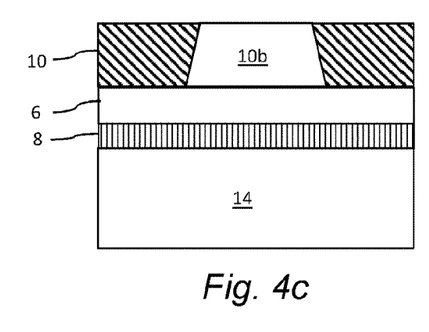
Figure 4D:
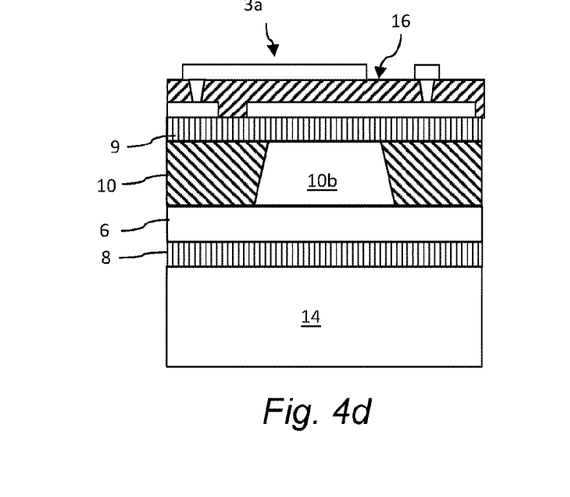
Figure 4E:
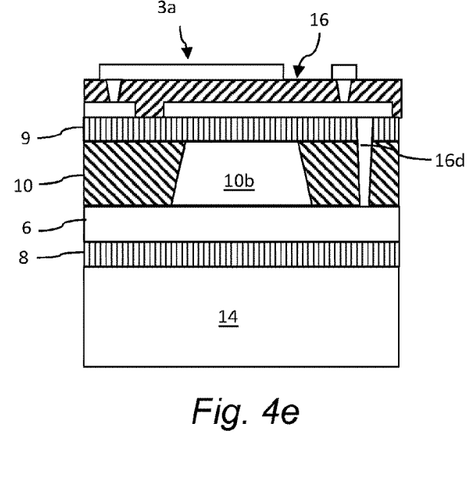
Figure 4F:
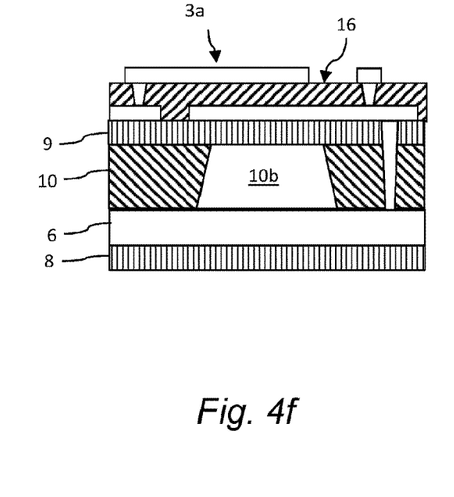

The bulk layer 10 with cavities 10b is formed on top of the second layer structure 6, as illustrated in FIG. 4c, and then the frontplane flexible layer 9 is delaminated from the second rigid substrate 15 and bonded axially on top of the bulk layer 10 with cavities 10b. Connections 16d from the piezoelectric element is fabricated through the frontplane flexible layer and the bulk layer to the second layer structure 6, thereby making a connection between the TFTs and the pMUT, as illustrated in FIG. 4e. Thereafter, the backplane flexible layer 8 is delaminated from the first rigid carrier substrate 14 to, thereby forming a flexible ultrasound transducer 1.

Figure 5A:
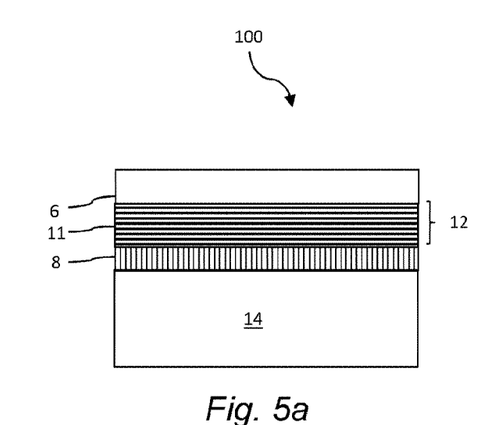
FIGS. 5a-f show an illustrative embodiment of a method for manufacturing a flexible ultrasound transducer.
Figure 5B:
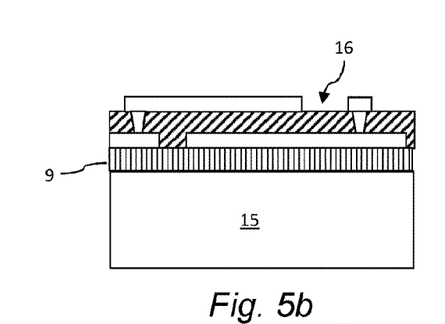
Figure 5C:
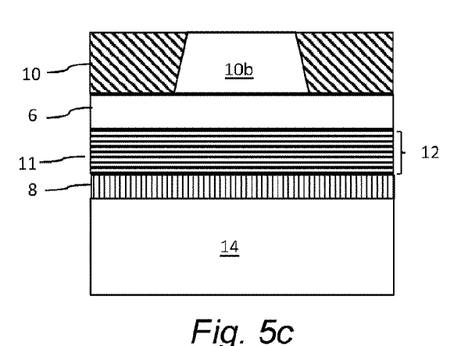
Figure 5D:
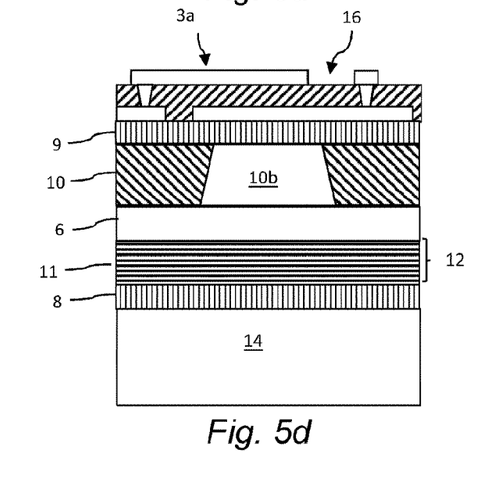
Figure 5E:
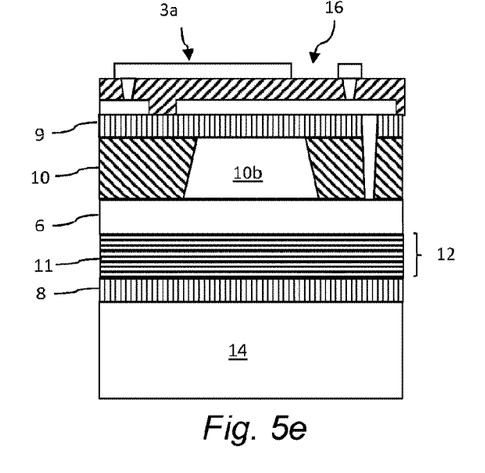
Figure 5F:
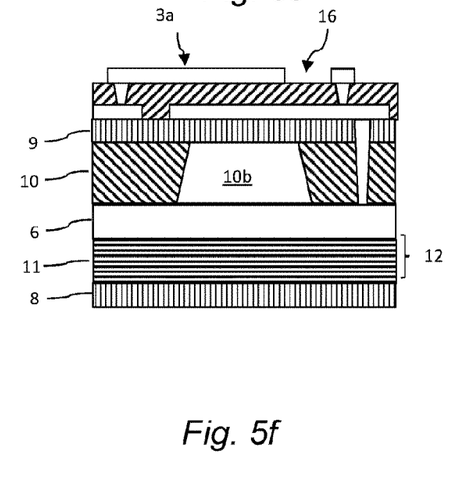

For both exemplary methods illustrated in FIGS. 3 and 4, an acoustic backing layer 11 as discussed herein above may be added in the flexible ultrasound transducer 1. An example is illustrated in FIGS. 5a-5f. This method is similar to the method discussed in relation to FIGS. 4a-f above, but an acoustic backing layer 11 in the form of a Bragg stack 12 is processed on top of the backplane flexible layer 8 before processing the second layer structure 6 on top of this Bragg stack 12, as illustrated in FIG. 5a. The Bragg stack comprises multiple layers of alternating high 12a and low 12b acoustic impedance materials as discussed above. The process then follows the same route, illustrated in FIGS. 5b-5f, as the example discussed in relation to FIG. 4 above.

Figure 7:
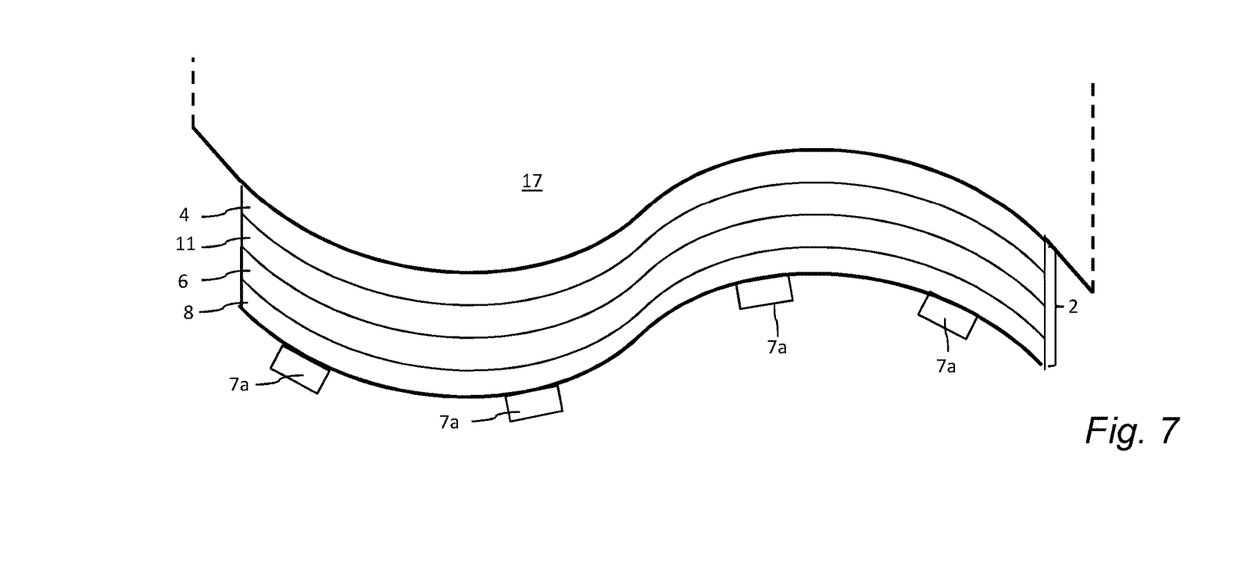
FIG. 7 schematically illustrates the flexible ultrasound transducer during examination of a curved object.

FIG. 7 schematically illustrates a flexible ultrasound transducer 1 during examination of a curved object 17, which may for example be an arm or a leg of a patient. Due to the incorporation of at least one flexible layer 8, the whole multi-layered structure 2 is flexible, thereby allowing the ultrasound transducer 1 to conform to the curved object 17. In this example, the whole multilayer structure 2 conforms to the curved object 17, whereas the individual ASICs 7a of the integrated circuit structure 7, arranged as discrete objects axially furthest away from the curved object 17 being examined, do not have to be bent.

Experimental Example

A substrate-cavity-flexible substrate-pMUT stack was created and delaminated from a rigid substrate and then again laminated onto a curved plastic substrate. It was found that the pMUT elements still worked after the steps of delamination and lamination onto the curved plastic substrate, with minor changes in the measured peak deflection of the pMUT elements. The results are summarized in Table 1 below:

TABLE 1

Measured peak deflection of pMUT elements before and after de- and relamination

| PMUT diameter [um] | Peak deflection before [um/s] | Peak deflection after [um/s] | FWHM BW before [kHz] | FWHM BW after [kHz] | Estimated resonance freq. in liquid (MHz) | Resonance freq. in air (MHz) |
|---|---|---|---|---|---|---|
| 240 | 574 ± 86 | 181 ± 60 | 39 ± 7 | 90 ± 52 | 0.625 | 1.25 |
| 300 | 761 ± 48 | 230 ± 86 | 19 ± 1 | 54 ± 34 | 0.425 | 0.85 |
| 400 | 835 ± 61 | 291 ± 232 | 12 ± 1 | 34 ± 23 | 0.25 | 0.5 |
| 600 | 847 ± 94 | 276 ± 198 | 5.8 ± 0.2 | 22 ± 15 | 0.125 | 0.25 |
| 800 | 535 ± 181 | 222 ± 172 | 4.3 ± 0.6 | 9.9 ± 10 | 0.1 | 0.2 |
| 1000 | 376 ± 181 | 321 ± 272 | 4.5 ± 1.4 | 15.6 ± 16.1 | 0.06 | 0.12 |

In the above the inventive concept has mainly been described with reference to a limited number of examples. However, as is readily appreciated by a person skilled in the art, other examples than the ones disclosed above are equally possible within the scope of the inventive concept, as defined by the appended claims.

The invention claimed is:

1. A flexible ultrasound transducer for an ultrasound monitoring system for examining a curved object, wherein said flexible ultrasound transducer comprises an integrated circuit structure and a multi-layered structure, said multi-layered structure comprising:
    an array of ultrasound transducing elements arranged in a first layer structure and configured for generating ultrasonic energy propagating along a main transducer axis Z; and
    an array of control circuits arranged in a second layer structure,
    wherein the array of control circuits and the integrated circuit structure are configured for operating the array of ultrasound transducing elements in said first layer structure;
    at least one flexible layer arranged so that the bending flexibility of the multi-layered structure permits the flexible ultrasound transducer to form a continuous contact with said curved object during operation; and
    an acoustic backing layer arranged axially below said first layer structure for reducing the acoustic transmission directed away from said curved object during operation,
    wherein the acoustic backing layer is an acoustic damping layer or an acoustic reflection layer in the form of a Bragg stack, wherein said Bragg stack comprises multiple layers of alternating high and low acoustic impedance materials.

2. The flexible ultrasound transducer according to claim 1, wherein each ultrasound transducing element in the array of ultrasound transducing elements of said first layer structure is connected with an individual control circuit of the array of control circuits of said second layer structure.

3. The flexible ultrasound transducer according to claim 1, wherein the second layer structure is arranged axially above a backplane flexible layer of the at least one flexible layer.

4. The flexible ultrasound transducer according to claim 1, wherein the integrated circuit structure comprises a plurality of Application Specific Integrated Circuits (ASIC), and wherein at least one ASIC supports a plurality of individual control circuits.

5. The flexible ultrasound transducer according to claim 3, wherein the integrated circuit structure comprises a plurality of Application Specific Integrated Circuits (ASIC), and wherein at least one ASIC supports a plurality of individual control circuits, and wherein said plurality of Application Specific Integrated Circuits (ASIC) are mounted as discrete elements axially below said backplane flexible layer.

6. The flexible ultrasound transducer according to claim 1, wherein the first layer structure comprises a frontplane flexible layer arranged between an array of piezoelements and a bulk layer, wherein said bulk layer comprises internal walls so as to define an array of cavities in the bulk layer, wherein an ultrasound transducing element in the array of ultrasound transducing elements is defined by one piezoelement of said array of piezoelements, a cavity of said array of cavities and a portion of the frontplane flexible layer that is arranged between the piezoelement and the cavity.

7. The flexible ultrasound transducer according to claim 1, wherein the array of control circuits comprises an array of thin film transistors (TFT).

8. The flexible ultrasound transducer according to claim 1, wherein the acoustic backing layer is arranged axially below said second layer structure.

9. The flexible ultrasound transducer according to claim 1, further comprising a top flexible layer arranged as an outermost layer axially above the first layer structure.

10. The flexible ultrasound transducer according to claim 1, wherein the multi-layered structure has a bending flexibility such that the flexible ultrasound transducer may be bent with a radius of curvature that is less than 5 cm.

11. A method for producing the flexible ultrasound transducer according to claim 1, the method comprising:
    a) arranging said second layer structure comprising the array of control circuits axially above a backplane flexible layer that is temporarily bonded to a first rigid substrate;
    b) arranging said first layer structure comprising the array of ultrasound transducing elements;
    c) forming the multi-layered structure of the flexible ultrasound transducer; and
    d) removing said first rigid substrate.

12. The method according to claim 11, wherein the first layer structure is built up on top of the second layer structure.

13. The method according to claim 11, wherein the first layer structure is temporarily bonded to a second rigid substrate, and wherein the method comprises removing said second rigid substrate before forming the multi-layered structure of the flexible ultrasound transducer.

* * * * *